(12) United States Patent
Fan et al.

(10) Patent No.: US 11,639,360 B2
(45) Date of Patent: May 2, 2023

(54) OXAZINE COMPOUND AND APPLICATION THEREOF

(71) Applicants: DALIAN UNIVERSITY OF TECHNOLOGY, Liaoning (CN); DALIAN CHROMAS BIOSCIENCE CO., LTD, Liaoning (CN)

(72) Inventors: Jiangli Fan, Liaoning (CN); Qichao Yao, Liaoning (CN); Haidong Li, Liaoning (CN); Yana Bian, Liaoning (CN); Mingle Li, Liaoning (CN); Jingyun Wang, Liaoning (CN); Xiaojun Peng, Liaoning (CN)

(73) Assignees: DALIAN UNIVERSITY OF TECHNOLOGY, Liaoning (CN); DALIAN CHROMAS BIOSCIENCE CO., LTD, Liaoning (CN)

( * ) Notice: Subject to any disclaimer, the term of this patent is extended or adjusted under 35 U.S.C. 154(b) by 0 days.

(21) Appl. No.: 17/053,042

(22) PCT Filed: Apr. 22, 2019

(86) PCT No.: PCT/CN2019/083615
§ 371 (c)(1),
(2) Date: Nov. 4, 2020

(87) PCT Pub. No.: WO2019/210786
PCT Pub. Date: Nov. 7, 2019

(65) Prior Publication Data
US 2021/0188875 A1 Jun. 24, 2021

(30) Foreign Application Priority Data
May 4, 2018 (CN) .................. 201810420618.1

(51) Int. Cl.
| | |
|---|---|
| C07D 517/16 | (2006.01) |
| A61P 35/00 | (2006.01) |
| A61K 9/14 | (2006.01) |
| A61K 41/00 | (2020.01) |
| C07D 513/16 | (2006.01) |
| C09K 11/06 | (2006.01) |
| G01N 21/64 | (2006.01) |

(52) U.S. Cl.
CPC .............. *C07D 517/16* (2013.01); *A61K 9/14* (2013.01); *A61K 41/0033* (2013.01); *A61K 41/0057* (2013.01); *A61P 35/00* (2018.01); *C07D 513/16* (2013.01); *C09K 11/06* (2013.01); *G01N 21/6428* (2013.01); *C09K 2211/1018* (2013.01); *G01N 2021/6439* (2013.01)

(58) Field of Classification Search
CPC ...... C07D 517/16; C07D 513/16; A61K 9/14; A61K 41/0033; A61K 41/0057; A61P 35/00; C09K 11/06; C09K 2211/1018; G01N 21/6428; G01N 2021/6439
See application file for complete search history.

(56) References Cited

FOREIGN PATENT DOCUMENTS

| | | |
|---|---|---|
| CN | 108774249 A | 11/2018 |
| JP | 2012126702 A | 7/2012 |

OTHER PUBLICATIONS

Leonard, Kristi , The design and Synthesis of Novel Chalcogenopyrulium Dyes as agents for Photodynamic Therapy, (2000), pp. 1-17 (Year: 2000).*
Yao, Qichao et al.; Differentiating RNA from DNA by a Molecular Fluorescent Probe Based on the "Door-bolt" Mechanism Biomaterials; Biomaterials, vol. 177, Sep. 30, 2018, pp. 78-87.
Kanitz, Andeas et al.; Preparation and Characterization of Bridged Naphthoxazinium Salts; European Journal of Drganic Chemistry; No. 4, Dec. 31, 1999, pp. 923-930.
Fang, Qian; The Synthesis and Properties of the Walter-soluble Benzo[a]phenoxazinium Chalcogen Analogues with Heteroatom (O, S, Se) as Photosensitizers; Chinese Master's Theses Full-Text Database, Engineering Science & Technology I; No. 03, Mar. 15, 2013, pp. B016-186.

* cited by examiner

*Primary Examiner* — Robert S Cabral
(74) *Attorney, Agent, or Firm* — Novick, Kim & Lee, PLLC; Allen Xue

(57) ABSTRACT

Disclosed are an oxazine compound and an application thereof. The oxazine compound has a structure of a general formula F. The oxazine compound described in the disclosure is a photo/acoustic dynamic active organic molecule with near-infrared absorption-emission function as well as photosensitivity and acoustic sensitivity. Maximum absorption and emission wavelengths of the compound are both greater than 660 nanometers, and a triplet-state conversion rate of the compound is high; and under illumination or ultrasound, the compound can produce reactive oxygen species with high efficiency, which has a good killing effect on cancer cells and cancer tissues, and almost has no toxic or side effects on normal tissues while achieving photo/acoustic dynamic therapy on tumors.

13 Claims, 7 Drawing Sheets

OXAZINE COMPOUND AND APPLICATION THEREOF

TECHNICAL FIELD

The disclosure belongs to the fields of anti-cancer drug design, synthesis and application. More particularly, the disclosure relates to synthesis of a novel oxazine photosensitizer/acoustic sensitizer as well as specific recognition of tumors and a new application in diagnosis and treatment of the novel oxazine photosensitizer/acoustic sensitizer.

BACKGROUND

A photodynamic action refers to a functional or morphologic change of an organism cell or a biomolecule under the action of light with the participation of a photosensitizer, which leads to cell injury and even necrosis in severe cases. In an early stage, oxygen is required to participate in the action, so that the action is also called photosensitization-oxidation action, which is called a photosensitization action in chemistry, and is called the photodynamic action in biology and medicine. A method of treating diseases by using the photodynamic action is called a photodynamic therapy (PDT). The photodynamic therapy is a new disease treatment method based on the interaction of the light, the photosensitizer and the oxygen, and the research of the photosensitizer (a photodynamic therapy drug) is a key to influence a prospect of the photodynamic therapy. The photosensitizer is composed of some special chemical substances, with a basic function of energy transfer. The photosensitizer can absorb photons so as to be excited, and then quickly transfers the absorbed light energy to molecules of another component, so that the molecules are excited while the photosensitizer itself returns to a ground state. With the approval of the first photosensitizer Porfimer Sodium in the United States, Canada, the European Union, Japan and South Korea from 1993 to 1997, the research, development and application of PDT became active quickly. With the successful development of new photodynamic therapy drugs and the improvement of laser equipment technology, PDT has ushered in an unprecedented development peak again. Internationally, nearly ten new photosensitizers have been approved or are being researched in clinic internationally. Meanwhile, PDT is also used for treating non-tumor diseases, such as condyloma acuminatum, psoriasis, nevus flammeus, rheumatoid arthritis, macular degeneration, restenosis after angioplasty and the like. Representative photosensitizers in China mainly include: ALA (5-ALA, Aminolevulinic Acid Hydrochloride for Topical Powder) developed and produced by Shanghai Fudan-zhangjiang Bio-Pharmaceutical Co., Ltd. In medical clinic and practice, dermatologists conveniently use ALA or PDT for short.

Ultrasound is used in a sonodynamic therapy (SDT) to penetrate through biological tissues. Particularly, focused ultrasound can noninvasively focus sound energy on deep tissues, and activate some acoustic-sensitive drugs (such as hematoporphyrin) to generate an anti-tumor effect. In 1990, Yumitai. q, et al. reported a synergistic effect of ultrasound combined with HP (hematoporphyrin) on growth inhibition of a transplanted tumor in a mouse, which showed that the single application of HP had no inhibitory effect, while the single application of ultrasound only had a slight inhibitory effect; however, the combination of the HP and the ultrasound has an obvious inhibitory effect, which was named sonodynamic therapy.

At present, porphyrins and phthalocyanine compounds are major representatives of photosensitizers/acoustic sensitizers applied in clinic. Although the compounds have achieved great success in tumor therapy, the compounds still have a plurality of defects, for example, the treatment system does not have a stable composition ratio, has a slow metabolism in a body, has a short maximum excitation wavelength, and is easy to cause phototoxic side effects. These defects seriously affect an actual effect and clinical application of the photodynamic therapy. There have already been some guiding thoughts internationally for the preparation and application of the photosensitizer, but there is no relevant theoretical guidance for the preparation and application of the acoustic sensitizer, and very few acoustic sensitizers can be applied in clinic. Therefore, designing a suitable photosensitizer/acoustic sensitizer will greatly promote the diagnosis and treatment of tumors.

SUMMARY

An objective of the disclosure is to develop a new compound with an oxazine foundation architecture and both photosensitivity and acoustic sensitivity at the same time. The compound should be able to take advantages of original characteristics of the oxazine compounds, such as high molar extinction coefficient, long absorption and emission wavelength, and oil/water amphipathy. Based on this, the new compound should also have outstanding functions of targeted identification, labeling and killing of tumor cells.

To this end, the disclosure firstly provides an oxazine compound having a structure of a general formula F:

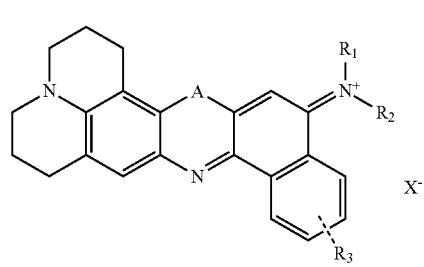

wherein, in the general formula F,

A is selected from sulfur (S), selenium (Se), and tellurium (Te);

$R_1$, $R_2$ and $R_3$ are each independently selected from hydrogen and substituted or unsubstituted $C_{1-20}$ alkyl;

the substituted alkyl is optionally substituted by the following groups: halogen, hydroxyl, alkoxy, aldehyde, carbonyl, amino, carboxyl, ester, acylamino, nitro or sulfonic acid group; and X is selected from phosphate radical, sulfate, bisulfate, nitrate, chlorine anion, bromine anion, iodine anion or perchlorate.

The oxazine compound described in the disclosure is a photo/acoustic dynamic active organic molecule with near-infrared absorption-emission function as well as photosensitivity and acoustic sensitivity. Maximum absorption and emission wavelengths of the compound are both greater than 660 nanometers, and a triplet-state conversion rate of the compound is high; and under illumination or ultrasound, the compound can produce reactive oxygen species with high efficiency, which has a good killing effect on cancer cells and cancer tissues, and almost does not increase any toxic or side effects on normal tissues while achieving photodynamic/sonodynamic therapy on tumors. Therefore, another aspect of the disclosure discloses an application of the oxazine compound in preparing a photosensitizer/acoustic sensitizer. The photosensitizer/acoustic sensitizer is a near-infrared long-wavelength fluorescent probe used for labeling tumor cells. The oxazine compound according to the disclosure may be used for micromolecule administration, and may also be self-assembled into nanoparticle or coated by other materials into nano ions for administration, and a nano-scale effective range is 1 to 1000 nanometers.

DETAILED DESCRIPTION

Figure 1:
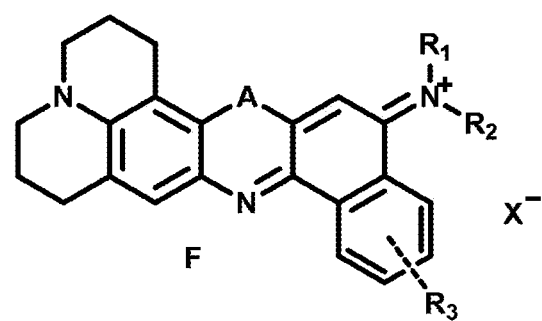
FIG. 1 shows a structural formula of a compound F-1.

The disclosure provides an oxazine compound having a structure of a general formula F:

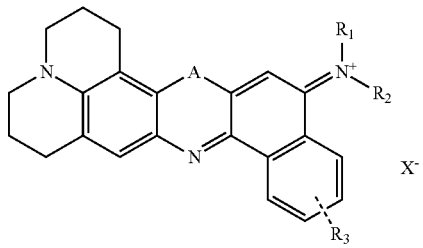

F wherein, in the general formula F,

A is selected from sulfur (S), selenium (Se), and tellurium (Te);

$R_1$, $R_2$ and $R_3$ are each independently selected from hydrogen and substituted or unsubstituted $C_{1-20}$ alkyl;

the substituted alkyl is optionally substituted by the following groups: halogen, hydroxyl, alkoxy, aldehyde, carbonyl, amino, carboxyl, ester, acylamino, nitro or sulfonic acid group; and X is selected from phosphate radical, sulfate, bisulfate, nitrate, chlorine anion, bromine anion, iodine anion or perchlorate.

In a specific technical solution, $R_1$, $R_2$ and $R_3$ in the general formula F are each independently selected from hydrogen and substituted or unsubstituted $C_{1-14}$ alkyl. Preferably, $R_1$, $R_2$ and $R_3$ in the general formula F are each independently selected from hydrogen and substituted or unsubstituted $C_{1-6}$ alkyl.

In a more specific technical solution, one of $R_1$ and $R_2$ in the general formula F is hydrogen. The feature may be combined with the technical feature that $R_3$ is hydrogen to form a further a preferred technical solution.

On the basis of further discriminating and comparing RNA specific recognition capabilities of each compound, in the most preferred embodiment provided by the disclosure, the following nine compounds are applied in preparing a near-infrared fluorescent probe, and the compound is selected from F-1, F-2, F-3, F-4, F-5, F-6, F-7, F-8, F-9, F-10 and F-11:

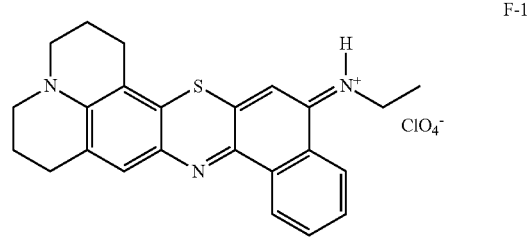

F-1

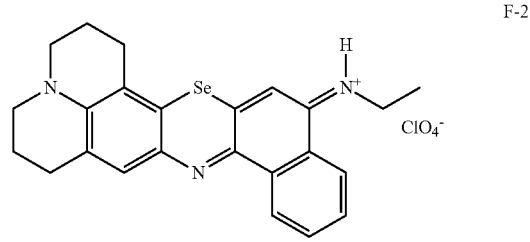

F-2

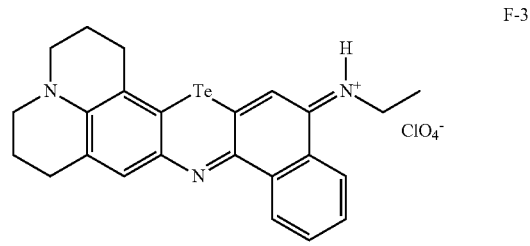

F-3

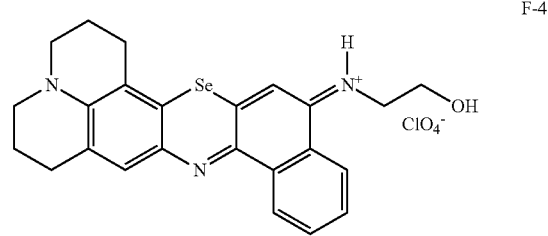

F-4

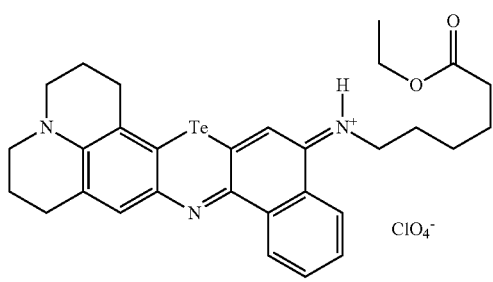

F-5

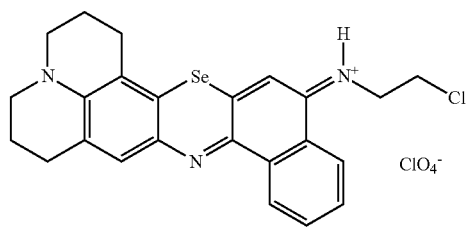

F-6

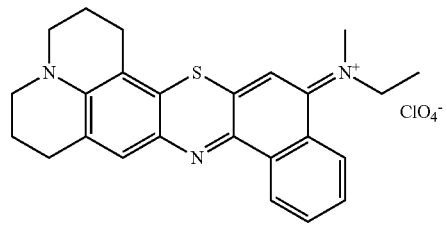

F-7

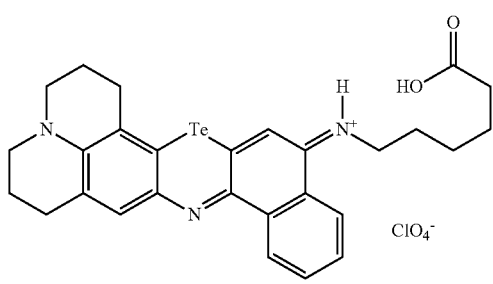

F-8

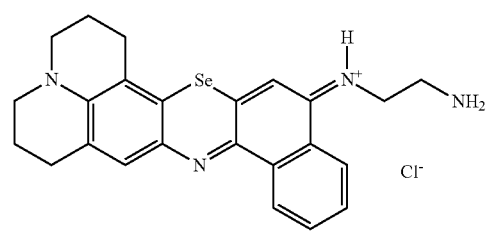

F-9

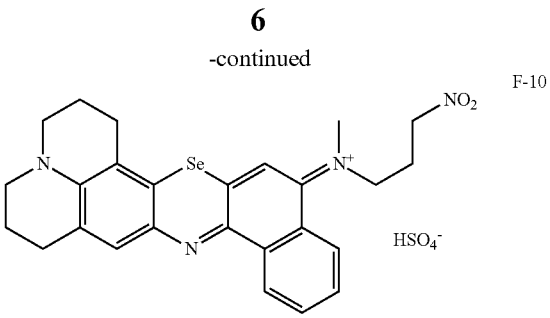

F-10

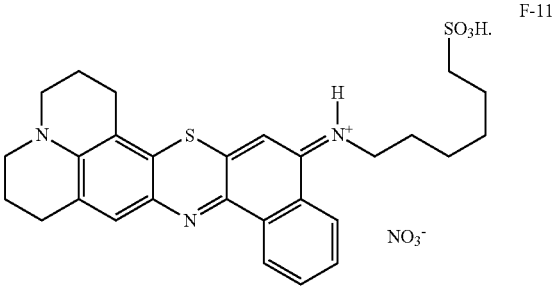

F-11

Unless otherwise specified, the terms used herein have the following meanings.

The term "alkyl" used herein includes a linear alkyl and a branched alkyl. If a single alkyl such as "propyl" is mentioned, it only refers to the linear alkyl in particular, and if a single branched alkyl such as "isopropyl" is mentioned, it only refers to the branched alkyl in particular. For example, "$C_{1-6}$ alkyl" includes $C_{1-4}$ alkyl, $C_{1-3}$ alkyl, methyl, ethyl, n-propyl, isopropyl and tert-butyl. Similar rules apply to other groups used in this specification.

The term "halogen" used herein includes halogens fluorine, chlorine, bromine, and iodine.

The preparation method of the compound with the general formula F mentioned above has not been disclosed by the prior art, and those skilled in the art should be able to complete the preparation of the compound according to the disclosure by combining the synthetic technology information in this specification and the basic theory and technology of organic synthesis. The following preparation method of the oxazine compounds described in this specification provides a specific solution for the synthesis of the compounds, but it should not be understood as a limitation to the synthesis of the compounds.

The oxazine compound described in the disclosure is synthesized through the following method: using an azo compound formed by aromatic amines or derivatives thereof to condense with 8-Hydroxyjulolidine in acid-containing DMF to prepare target oxazine dyes. The synthesis method has simple process and high conversion rate. More specifically, a synthetic route of the compound of the general formula F of the disclosure is as follows:

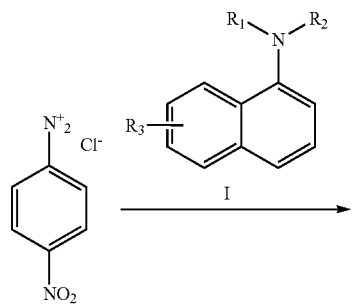

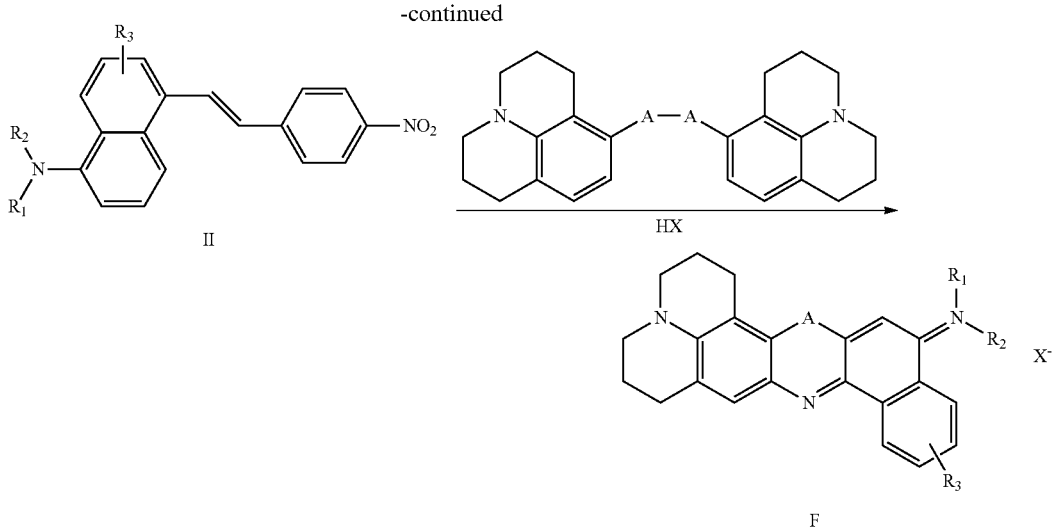

The preparation method of the compound of the general formula F represented by the above-mentioned route includes the following steps:

(1) in a hydrochloric acid acidification system, reacting p-nitrodiazobenzene chloride a compound of formula I according to a molar ratio of 1:1 at 25 to 35° C. for 0.5 to 2 hours to prepare a compound of formula II; and

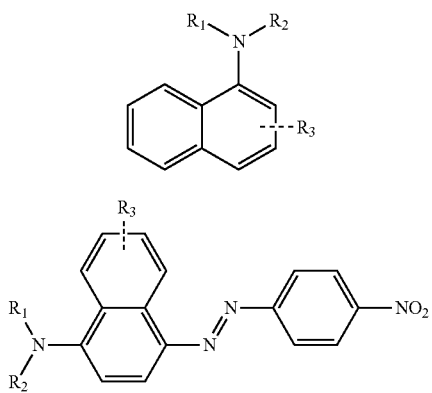

(2) reacting the compound of formula II with 8-Hydroxyjulolidine according to a molar ratio of 1:1 in acidic DMF at 135 to 145° C. for 2 to 4 hours to prepare the compound of formula F.

The photosensitizer/acoustic sensitizer with oxazine as a parent according to the disclosure has the following characteristics:

(1) the photosensitizer/acoustic sensitizer has certain water solubility and excellent cell membrane permeability;

(2) the photosensitizer/acoustic sensitizer has excellent near-infrared emission characteristics, which has photobleaching, photodamage and phototoxicity when being applied to biological imaging, and a generated fluorescence signal can penetrate deep biological tissues;

(3) under the illumination of 700 nanometers wavelength or ultrasound, a large amount of singlet oxygen can be produced; and (4) under test conditions, the photosensitizer/acoustic sensitizer has low dark toxicity, good biocompatibility, certain water solubility and good photostability, and may be used as an excellent photosensitizer in photodynamic and sonodynamic tumor therapy fields.

According to the disclosure, oxygen heavy elements are introduced into therapeutic molecules, so that the molecules have various advantages of photodynamic therapy, sonodynamic therapy and chemotherapy at the same time, and can diagnose and treat tumors more efficiently. Moreover, the compound provided by the disclosure has simple and stable molecular structure and small toxic or side effects. The compound provided by the disclosure is easy to prepare and purify, and the raw materials are readily available, which has great advantages for the industrialized production of drugs for photodynamic and sonodynamic tumor therapy.

On the basis of the above-mentioned features, the near-infrared photosensitizer/acoustic sensitizer according to the disclosure may be used for labeling tumor and non-tumor cells and tissues. In addition to being directly used for staining and labeling the tumor and non-tumor cells and tissues in the form described herein, a composition containing the near-infrared fluorescent probe compound of the disclosure may also be used for staining and labeling the tumor cells and tissues. The composition should contain an effective amount of one of the two-photon fluorescence probe compounds provided by the disclosure. Moreover, the composition may also contain other components required for staining biological samples, such as solvents, pH regulators, etc. These components are known in the industry. The above composition may exist in the form of an aqueous solution, or may exist in other suitable forms where water is used to prepare a solution.

The disclosure further provides a method of using the above near-infrared photosensitizer/acoustic sensitizer of the disclosure to label the tumor cells and tissues and the biological samples. The method includes a step of enabling the compound to be contacted with the biological samples. The term "contact" used herein may include contacting in a solution or a solid phase.

The following non-limiting embodiments enable those of ordinary skills in the art to understand the disclosure more fully, but do not limit the disclosure in any way.

Embodiment 1: Preparation of Compound F-1

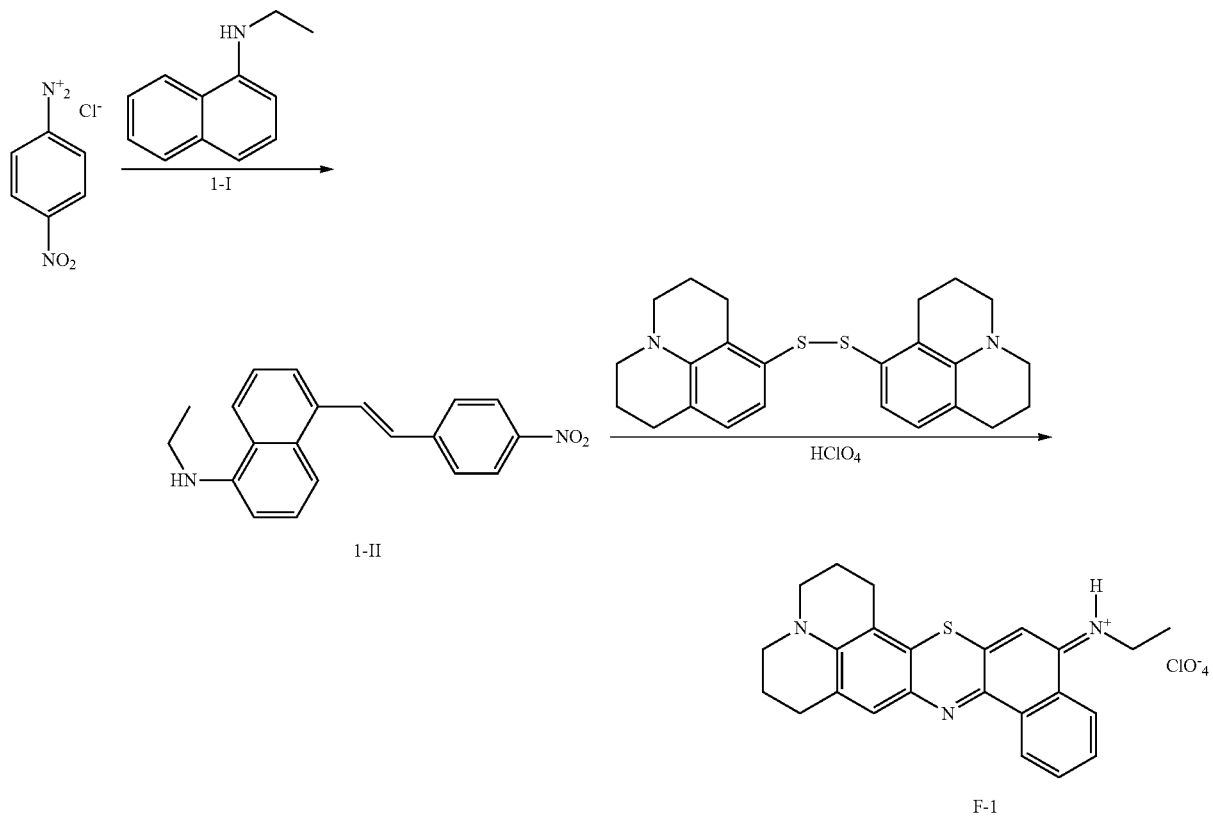

(1) Synthesis of Intermediate 1-II

In a hydrochloric acid acidification system, p-nitrodiazobenzene chloride reacted with a compound of 1-I according to a molar ratio of 1:1 at 25 to 35° C. for 0.5 to 2 hours. After the reaction was completed, a brick-red solid powder crude product was obtained after filtration and washing operation, and the compound of formula 1-II was obtained with a yield of 95%.

(2) Synthesis of Compound F-1

The intermediate 1-II prepared in the above reaction (1) and sulfydryljulolidine were added into a round-bottom flask containing DMF, and then 1 mL of perchloric acid solution was dropped in. After dropping, the reaction was stopped after the system was stirred for 2.5 hours, and the remaining was separated by silica gel column chromatography, and then eluted and purified by dichloromethane and methanol with a ratio (v:v) of 8:1 to obtain the dark blue target compound F-1 (structural formula shown in FIG. 1) with metallic luster needle-like crystals and a yield of 83.2%.

$^1$H NMR (400 MHz, DMSO) δ 9.13 (s, 1H), 8.77 (d, J=8.2 Hz, 1H), 8.34 (d, J=8.1 Hz, 1H), 7.84 (t, J=7.4 Hz, 1H), 7.77 (t, J=7.5 Hz, 1H), 7.44 (s, 1H), 7.22 (s, 1H), 3.54 (d, J=17.3 Hz, 5H), 2.96-2.71 (m, 3H), 2.49 (s, 6H), 2.05-1.99 (m, 2H), 1.98-1.92 (m, 2H), 1.35 (t, J=7.2 Hz, 3H).

Embodiment 2: Spectral Test Experiment of Compound F-1

Figure 2:
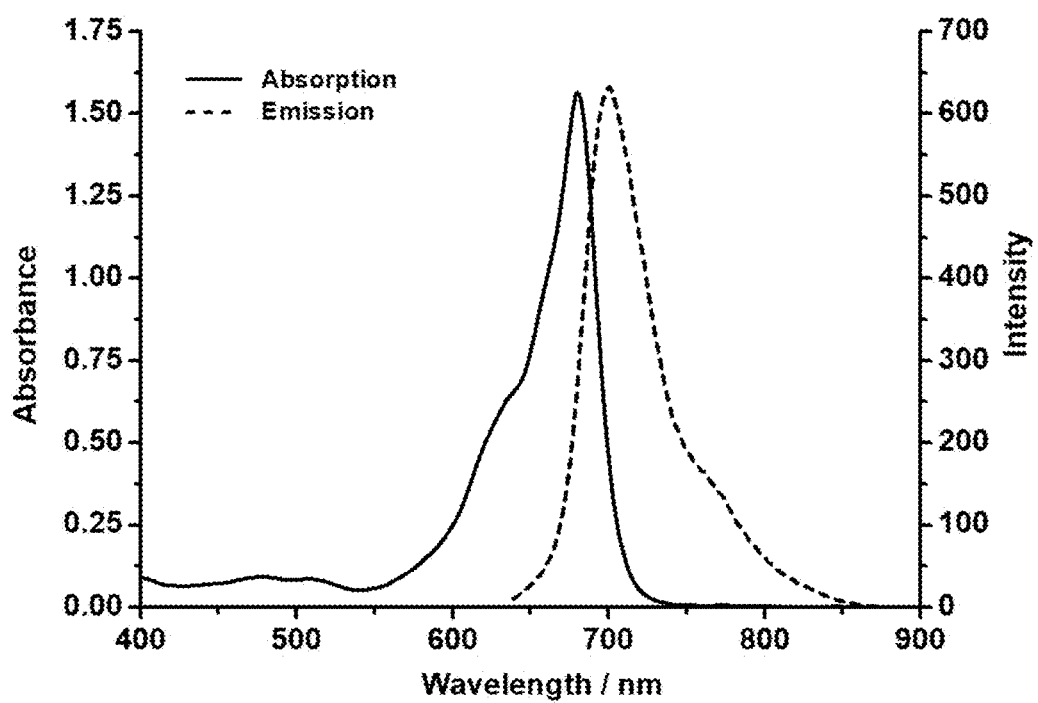
FIG. 2 shows results of a spectral test experiment of the compound F-1 (Embodiment 2).

The compound F-1 synthesized in Embodiment 1 was used, and F-1-DMSO solution was added into dichloromethane and mixed evenly. Spectral properties of the compound F-1 were tested by a UV-vis spectrophotometer and a fluorescence spectrometer. The results are shown in FIG. 2, wherein the F-1 molecules have the maximum absorption and the maximum emission at 680 nanometers and 700 nanometers in the dichloromethane respectively.

Figure 3:
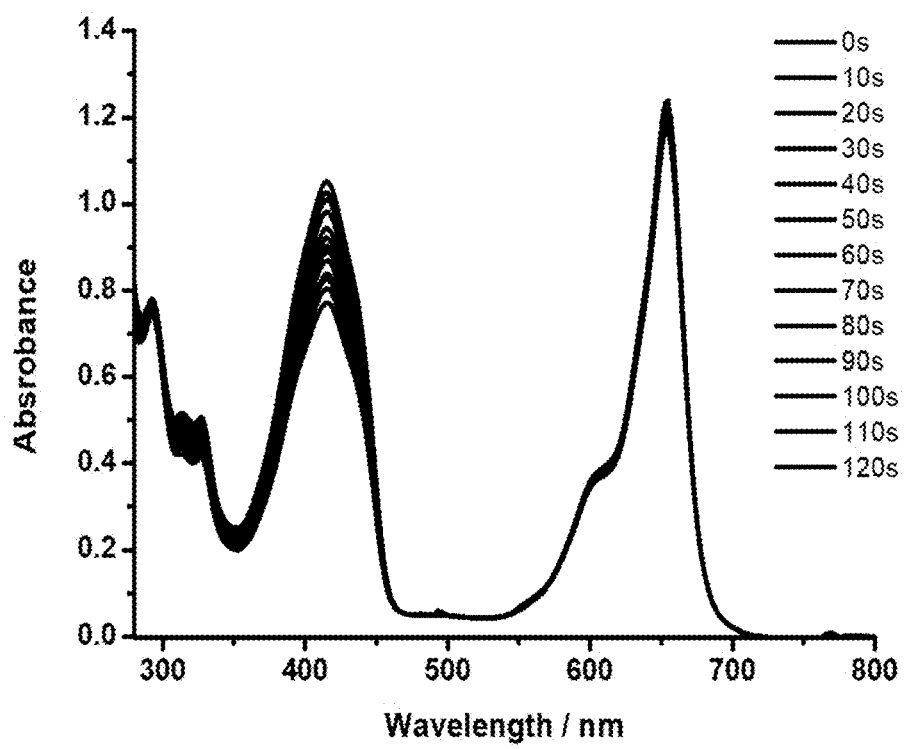
FIG. 3 shows results of a singlet oxygen yield determination experiment of the compound F-1 under illumination (Embodiment 3).

Embodiment 3: Singlet Oxygen Yield Determination Experiment of Compound F-1 Under Illumination The compound F-1 synthesized in Embodiment 1 was used, and F-1-DMSO solution was added into methanol and mixed evenly, then 1,3-Diphenylisobenzofuran (DPBF) was added, and a concentration of DPBF was adjusted till an absorbance value of DPBF was about 1.0, then a xenon lamp light source with a wavelength of 660 nanometers (adjusted by grating filter) was used to irradiate, and a UV-vis absorption curve of the system was measured at equal time intervals. A correlation curve between the absorbance and the time was drawn according to changes of the absorbance of DPBF at a wavelength of 411 nanometers, and a singlet oxygen proton yield of the compound F-1 was calculated by using methylene blue as a reference. The results are shown in FIG. 3. The figure shows changes of a UV-vis absorption spectrum of the mixed system with the extension of illumination time. According to a relevant formula, the singlet oxygen photon yield of the compound F-1 is about 0.018.

Figure 4:
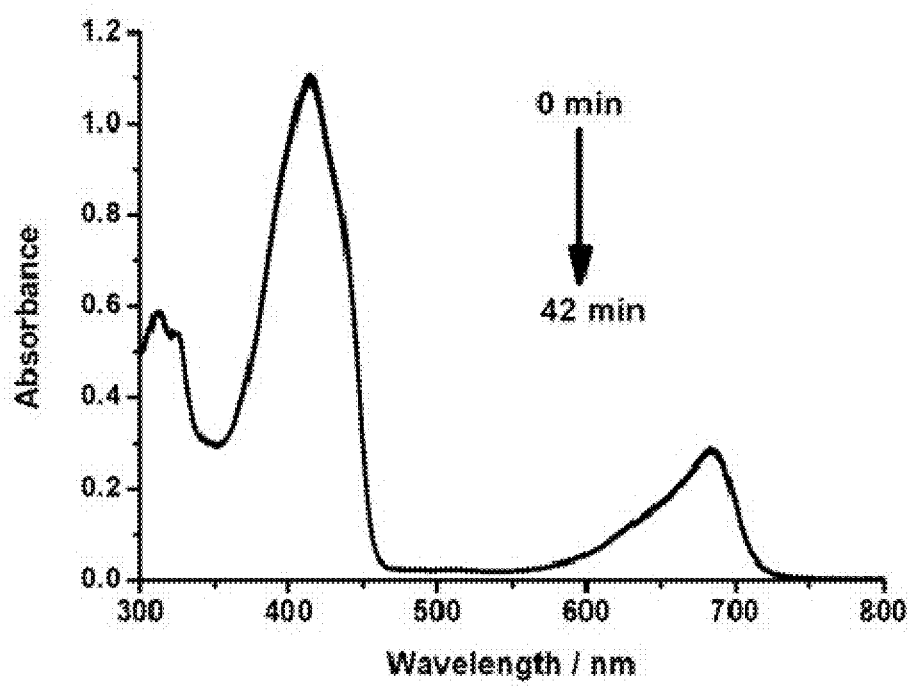
FIG. 4 shows results of an in vitro cell anti-cancer test experiment of the compound F-1 under ultrasound (Embodiment 4).

Embodiment 4: Singlet Oxygen Yield Determination Experiment of Compound F-1 Under Ultrasound The compound F-1 synthesized in Embodiment 1 was used, and F-1-DMSO solution was added into ethylene glycol monomethyl ether and mixed evenly, then 1,3-Diphenylisobenzofuran (DPBF) was added, and a concentration of DPBF was adjusted till an absorbance value of DPBF was about 1.0, then ultrasound was used to circularly simulate (1.5 W/cm$^2$, 50% duty cycle), and a ultraviolet-visible absorption curve of the system was measured at equal time intervals. A correlation curve between the absorbance and the time was drawn according to changes of the absorbance of DPBF at a wavelength of 411 nanometers, and the results are shown in FIG. 4. The figure shows changes of a UV-vis absorption spectrum of the mixed system with the extension of ultrasound time. It can be known from the figure that the compound F-1 can generate the singlet oxygen under the promotion of ultrasound.

Embodiment 5: In Vitro Cell Anti-Cancer Test of Compound F-1 Under Illumination

MCF-7 (human breast cancer cell) was planted in 96-well culture plates at a density of 5000 cells per well and cultured in a cell incubator for 24 hours (37° C., 5% CO$_2$). The compound F-1 synthesized in Embodiment 1 was used, and F-1-DMSO solution was added into DMEM containing 10% fetal calf serum to prepare solutions with different concentrations, and the prepared solutions were added to the 96-well culture plates and placed in a cell incubator to incubate for 30 minutes, and then irradiated for a certain period by red light with a wavelength of 660 nanometers. After irradiation, 96 empty plates were placed in a cell incubator and continuously incubated for 12 hours. Then, 100 μl of culture medium containing 5 mg/ml MTT was added to each well, and incubated in a cell incubator for 4 hours. The culture solutions in the well of the plates were removed, 100 l of DMSO was added to each well to fully dissolve MTT oxidation products, and then the absorbance of each well at 570 nanometers and 630 nanometers were measured with a microplate reader, and a cell survival rate was calculated. The results are shown in FIG. 5.

Figure 5:
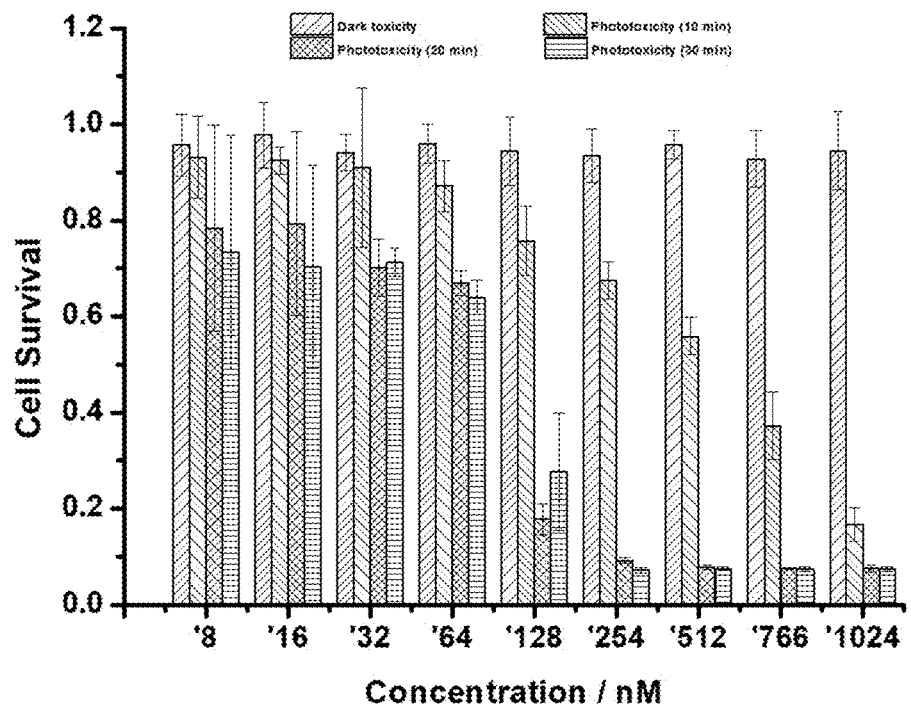
FIG. 5 shows results of an in vitro cell anti-cancer test experiment of the compound F-1 under illumination (Embodiment 5).

It can be seen from FIG. 5 that the compound F-1 has a very small killing effect on the cells without illumination, and has almost no toxicity; under illumination, the compound F-1 can produce an obvious killing effect on the cells, and the phototoxicity of the compound F-1 increases significantly with the increase of an energy density of illumination.

Embodiment 6: Preparation of Compound F-2

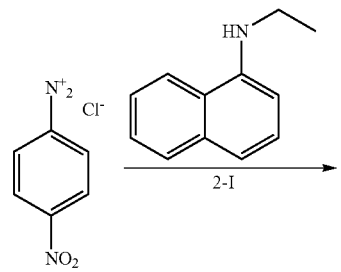

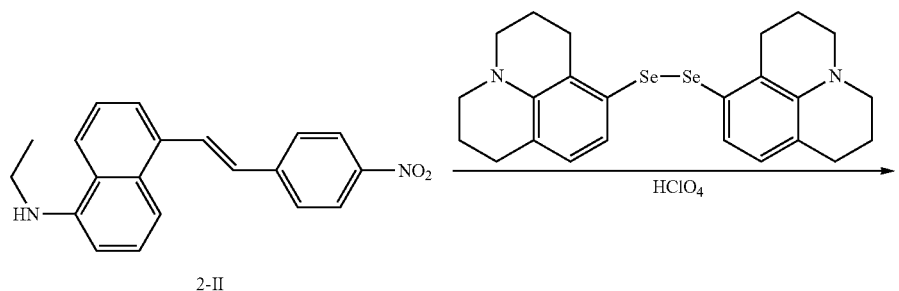

2-II

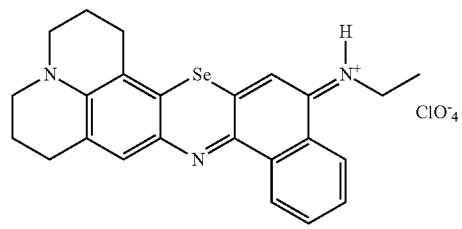

F-2

(1) Synthesis of Intermediate 2-II

In a hydrochloric acid acidification system, p-nitrodiazobenzene chloride reacted with a compound of 2-I according to a molar ratio of 1:1 at 25 to 35° C. for 0.5 to 2 hours. After the reaction was completed, a brick-red solid powder crude product was obtained after filtration and washing operation, and the compound of formula 2-II was obtained with a yield of 95%.

(2) Synthesis of Compound F-2

The intermediate 2-II prepared in the above reaction (1) and selenojulolidine were added into a round-bottom flask containing DMF, and then 1 mL of perchloric acid solution was dropped in. After dropping, the reaction was stopped after the system was stirred for 2.5 hours, and the remaining was separated by silica gel column chromatography, and then eluted and purified by dichloromethane and methanol with a ratio (v:v) of 8:1 to obtain the dark blue target compound F-2 with metallic luster needle-like crystals and a yield of 54.4%.

1H NMR (400 MHz, DMSO) δ 9.26 (s, 1H), 8.91 (d, J=7.7 Hz, 1H), 8.40 (d, J=8.0 Hz, 1H), 7.90-7.74 (m, 2H), 7.67 (d, J=21.0 Hz, 2H), 3.65-3.46 (m, 6H), 3.30 (s, 3H), 2.88 (s, 2H), 2.02 (d, J=38.7 Hz, 4H), 1.36 (t, J=6.8 Hz, 3H).

Embodiment 7: Spectral Test Experiment of Compound F-2

Figure 6:
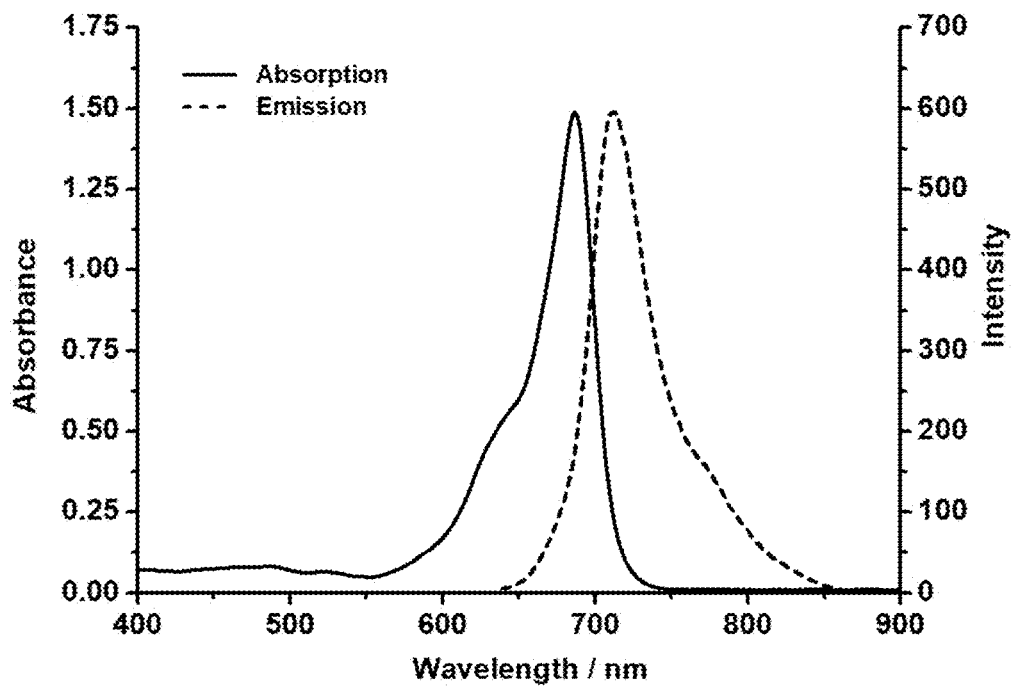
FIG. 6 shows results of a spectral test experiment of a compound F-2 (Embodiment 7).

The compound F-2 synthesized in Embodiment 6 was used, and F-2-DMSO solution was added into dichloromethane and mixed evenly. Spectral properties of the compound F-1 were tested by a UV-vis spectrophotometer and a fluorescence spectrometer. The results are shown in FIG. 6, wherein the F-2 molecules have the maximum absorption and the maximum emission at 686 nanometers and 712 nanometers in the dichloromethane are respectively.

Figure 7:
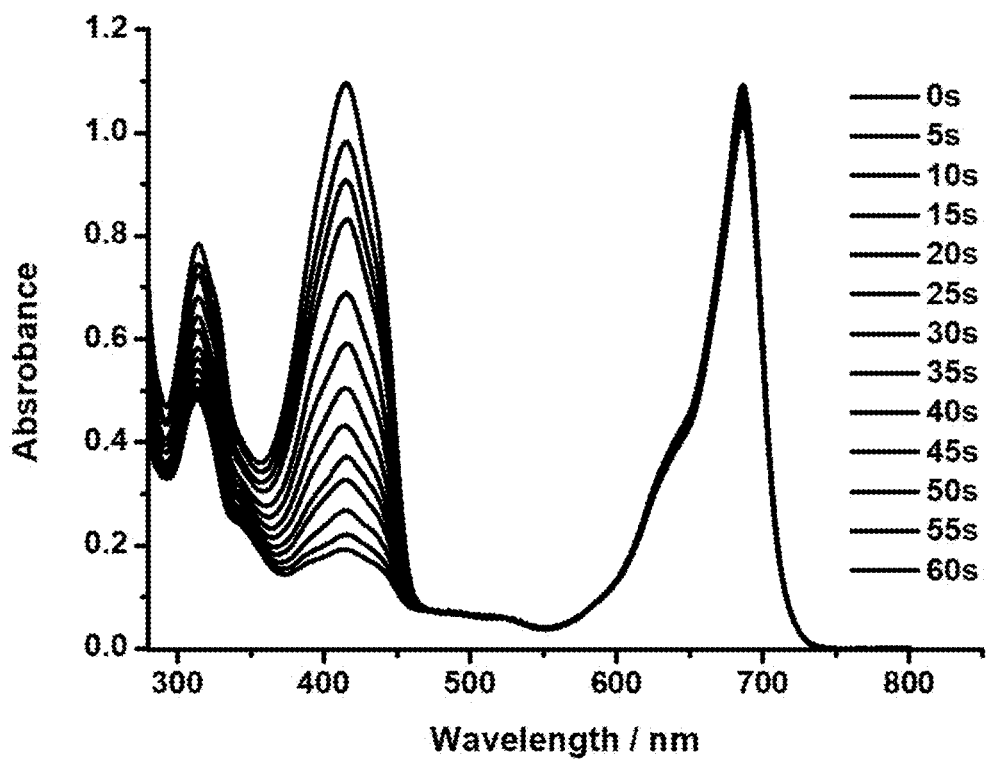
FIG. 7 shows results of a singlet oxygen yield determination experiment of the compound F-2 under illumination (Embodiment 8).

Embodiment 8: Singlet Oxygen Yield Determination Experiment of Compound F-2 Under Illumination The compound F-2 synthesized in Embodiment 6 was used, and F-2-DMSO solution was added into methanol and mixed evenly, then 1,3-Diphenylisobenzofuran (DPBF) was added, and a concentration of DPBF was adjusted till an absorbance value thereof was about 1.0, then a xenon lamp light source with a wavelength of 660 nanometers (adjusted by grating filter) was used to irradiate, and a ultraviolet-visible absorption curve of the system was measured at equal time intervals. A correlation curve between the absorbance and the time was drawn according to changes of the absorbance of DPBF at a wavelength of 411 nanometers, and a singlet oxygen proton yield of the compound F-2 was calculated by using methylene blue as a reference. The results are shown in FIG. 7. The figure shows changes of a UV-vis absorption spectrum of the mixed system with the extension of illumination time. According to a relevant formula, the singlet oxygen photon yield of the compound F-2 is about 0.47.

Figure 8:
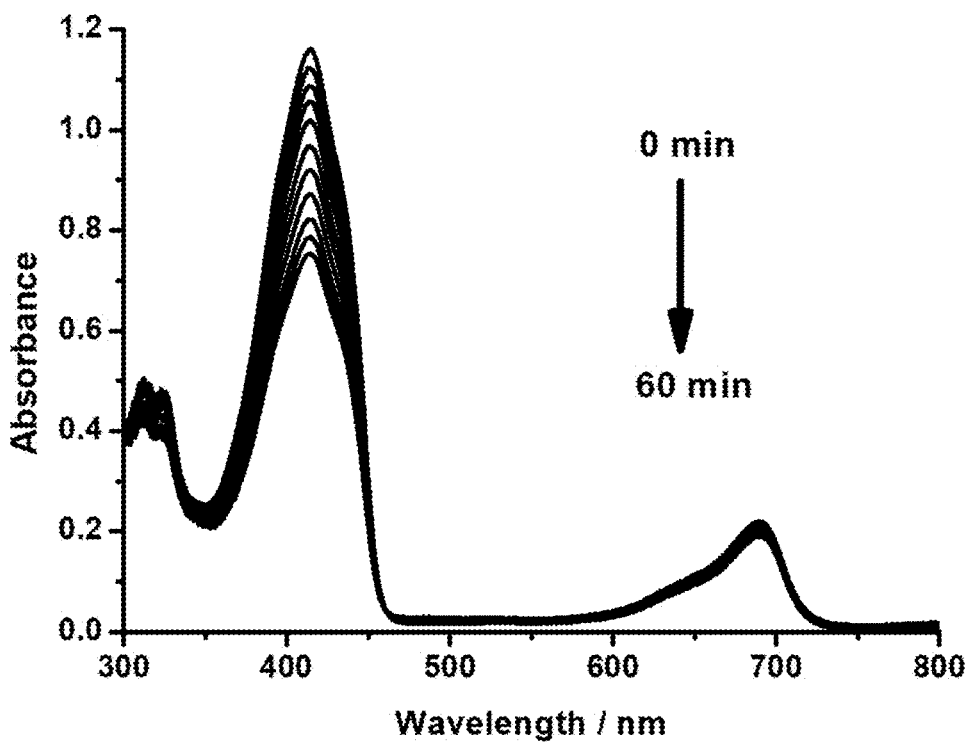
FIG. 8 shows results of a singlet oxygen yield determination experiment of the compound F-2 under ultrasound (Embodiment 9).

Embodiment 9: Singlet Oxygen Yield Determination Experiment of Compound F-2 Under Ultrasound The compound F-2 synthesized in Embodiment 6 was used, and F-2-DMSO solution was added into ethylene glycol monomethyl ether and mixed evenly, then 1,3-Diphenylisobenzofuran (DPBF) was added, and a concentration of DPBF was adjusted till an absorbance value of DPBF was about 1.0, then ultrasound was used to circularly simulate (1.5 W/cm$^2$, 50% duty cycle), and a ultraviolet-visible absorption curve of the system was measured at equal time intervals. A correlation curve between the absorbance and the time was drawn according to changes of the absorbance of DPBF at a wavelength of 411 nanometers, and the results are shown in FIG. 8. The figure shows changes of a UV-vis absorption spectrum of the mixed system with the extension of ultrasound time. It can be seen that the compound F-2 can generate the singlet oxygen under the promotion of ultrasound.

Embodiment 10: In Vitro Cell Anti-Cancer Test of Compound F-2 Under Illumination MCF-7 (human breast cancer cell) was planted in 96-well culture plates at a density of 5000 cells per well and cultured in a cell incubator for 24 hours (37° C., 5% CO$_2$). The compound F-2 synthesized in Embodiment 6 was used, and F-2-DMSO solution was added into DMEM containing 10% fetal calf serum to prepare solutions with different concentrations, and the prepared solutions were added to the 96-well culture plates and placed in the cell incubator to incubate for 30 minutes, and then irradiated for a certain period by red light with a wavelength of 660 nanometers. After irradiation, 96 empty plates were placed in a cell incubator and continuously incubated for 12 hours. Then, 100 μl of culture medium containing 5 mg/ml MTT was added to each well, and incubated in a cell incubator for 4 hours. The culture solutions in the well of the plates were removed, 100 l of DMSO was added to each well to fully dissolve MTT oxidation products, and then the absorbance of each well at 570 nanometers and 630 nanometers were measured with a microplate reader, and a cell survival rate was calculated. The results are shown in FIG. 9.

Figure 9:
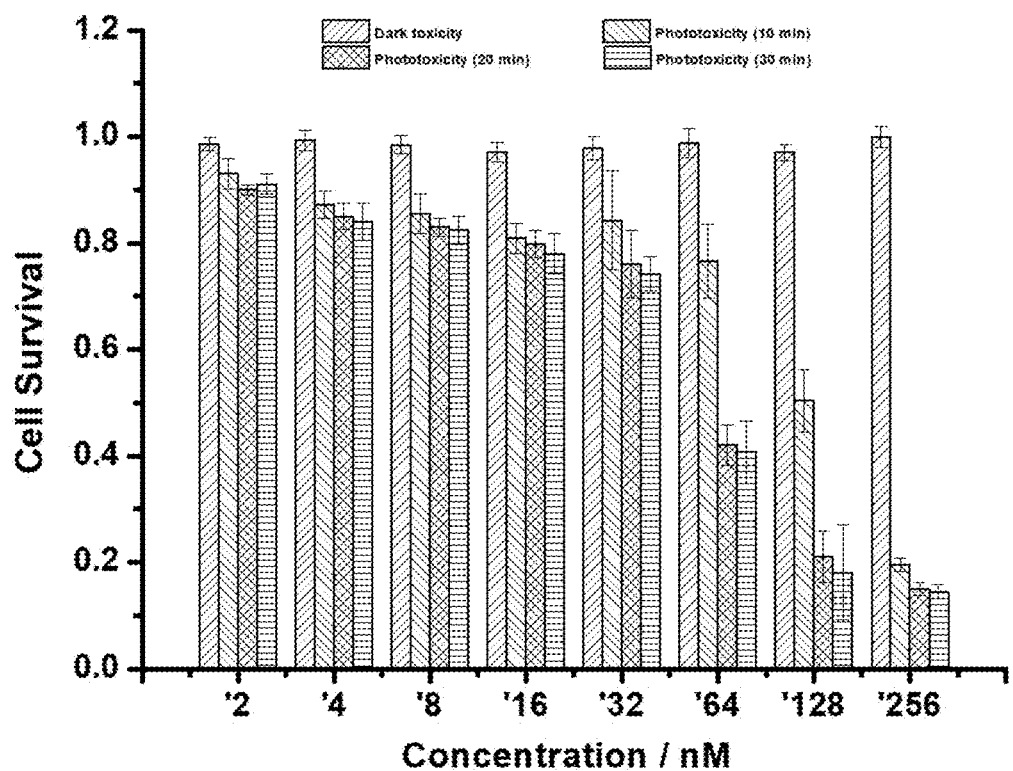
FIG. 9 shows results of an in vitro cell anti-cancer test experiment of the compound F-2 under illumination (Embodiment 10).

It can be seen from FIG. 9 that the compound F-2 has a very small killing effect on the cells without illumination, and has almost no toxicity; and under illumination, the compound F-2 can produce an obvious killing effect on the cells at low energy density of illumination.

Embodiment 11: Preparation of Compound F-3

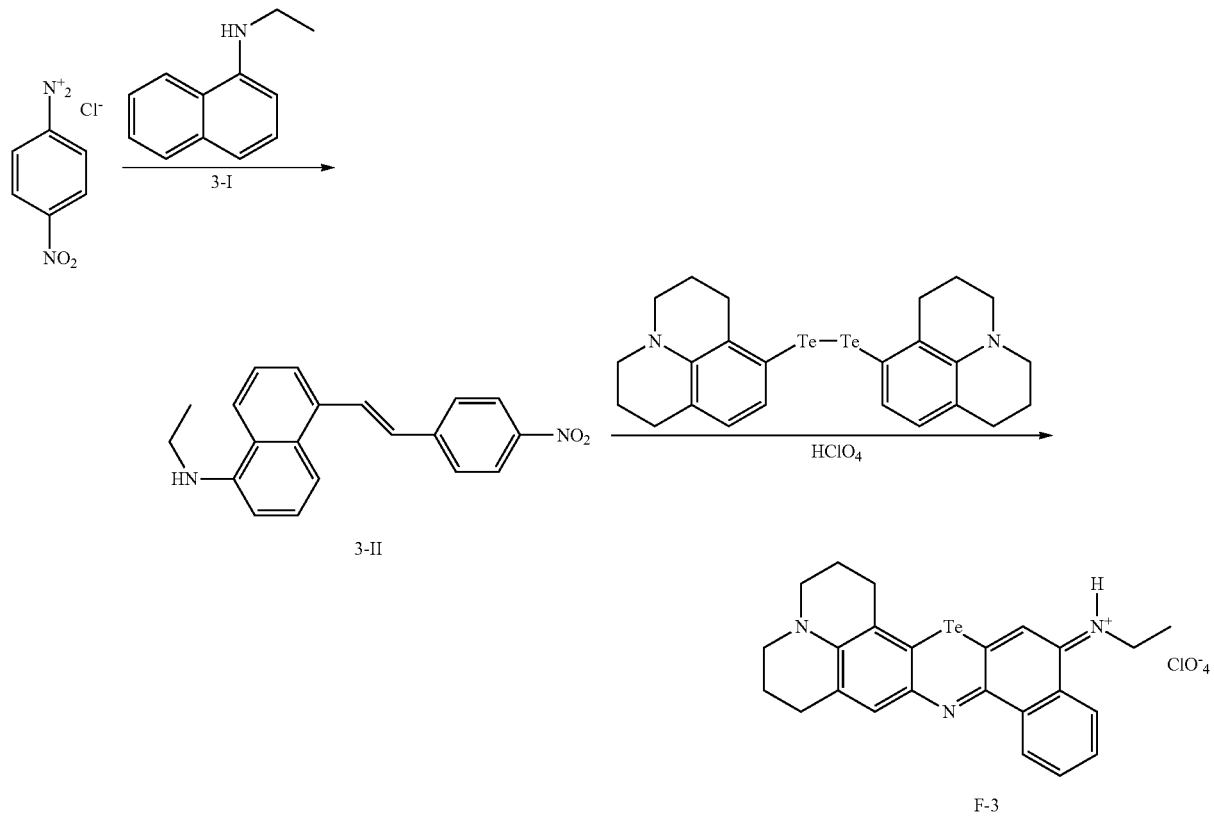

(1) Synthesis of Intermediate 3-II

In a hydrochloric acid acidification system, p-nitrodiazobenzene chloride reacted with a compound of 3-I according to a molar ratio of 1:1 at 25 to 35° C. for 0.5 to 2 hours. After the reaction was completed, a brick-red solid powder crude product was obtained after filtration and washing operation, and the compound of formula 3-II was obtained with a yield of 94%.

(2) Synthesis of Compound F-3

The intermediate 3-II prepared in the above reaction (1) and telluricjulolidine were added into a round-bottom flask containing DMF, and then 1 mL of perchloric acid solution was dropped in. After dropping, the reaction was stopped after the system was stirred for 2.5 hours, and the remaining was separated by silica gel column chromatography, and then eluted and purified by dichloromethane and methanol with a ratio (v:v) of 8:1 to obtain the dark blue target compound F-3 with metallic luster needle-like crystals and a yield of 65.9%.

$^1$H NMR (400 MHz, DMSO) δ 9.13 (s, 1H), 8.90 (d, J=8.1 Hz, 1H), 8.36 (d, J=8.1 Hz, 1H), 8.07 (s, 1H), 7.80 (t, J=7.5 Hz, 1H), 7.74 (t, J=7.4 Hz, 1H), 7.66 (s, 1H), 3.54 (dd, J=13.7, 6.7 Hz, 2H), 3.43 (d, J=5.0 Hz, 4H), 2.90-2.75 (m, 2H), 2.35 (t, J=6.1 Hz, 2H), 2.07-2.00 (m, 2H), 1.98-1.86 (m, 3H), 1.36 (t, J=7.2 Hz, 3H).

Embodiment 12: Spectral Test Experiment of Compound F-3

Figure 10:
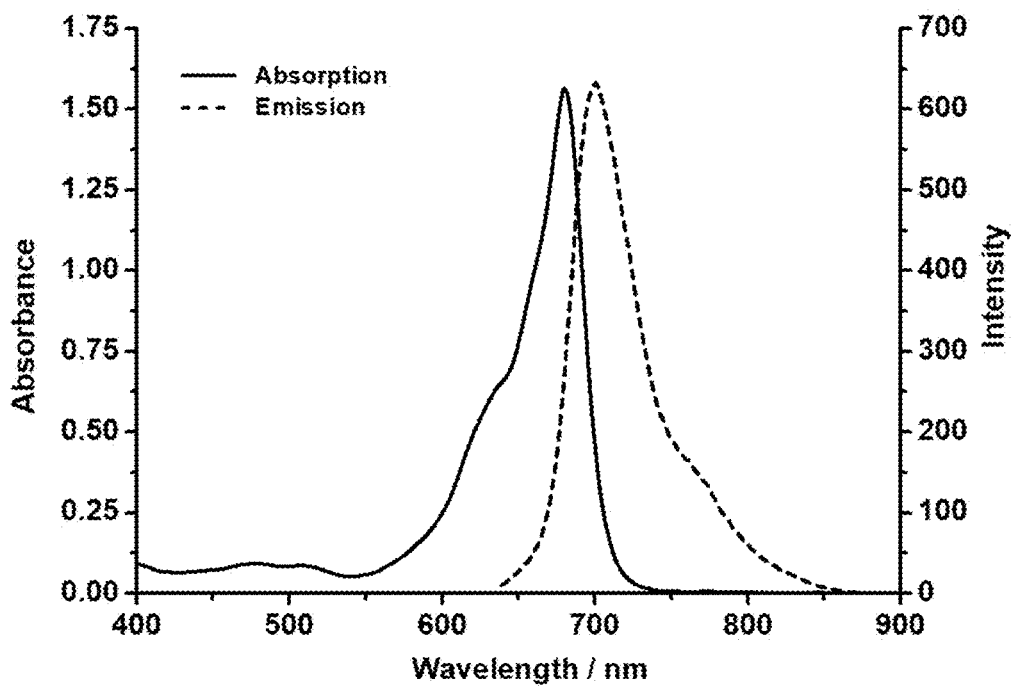
FIG. 10 shows results of a spectral test experiment of a compound F-3 (Embodiment 12).

The compound F-3 synthesized in Embodiment 11 was used, and F-3-DMSO solution was added into dichloromethane and mixed evenly. Spectral properties of the compound F-1 were tested by a UV-vis spectrophotometer and a fluorescence spectrometer. The results are shown in FIG. 10, wherein the F-3 molecules have the maximum absorption and the maximum emission at 697 nanometers and 740 nanometers in the dichloromethane.

Figure 11:
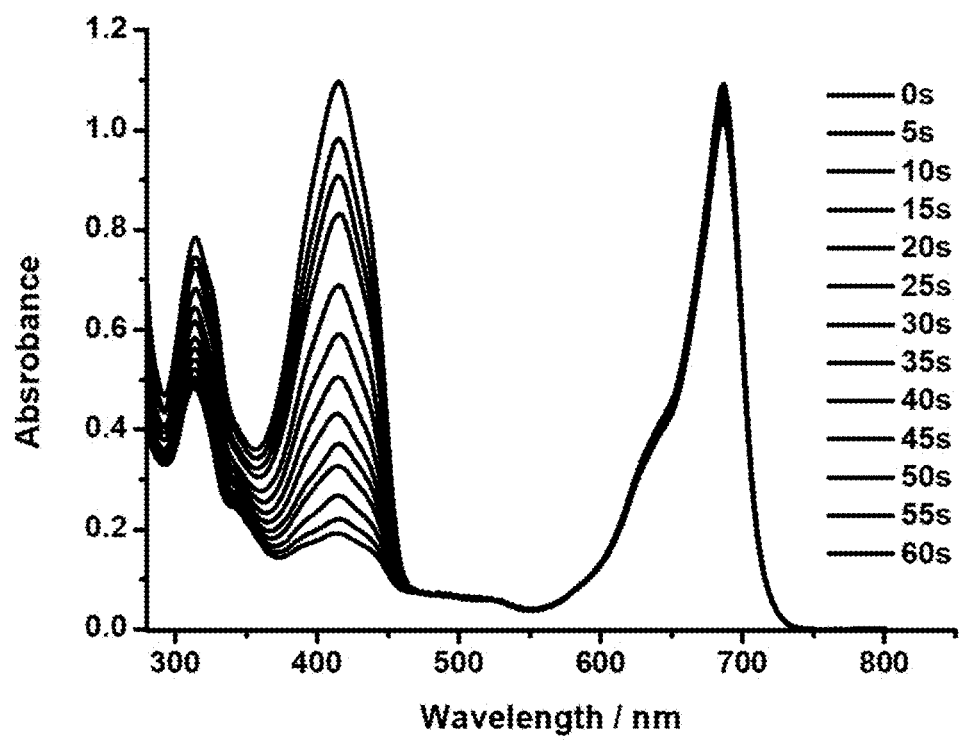
FIG. 11 shows results of a singlet oxygen yield determination experiment of the compound F-3 under illumination (Embodiment 13).
Figure 12:
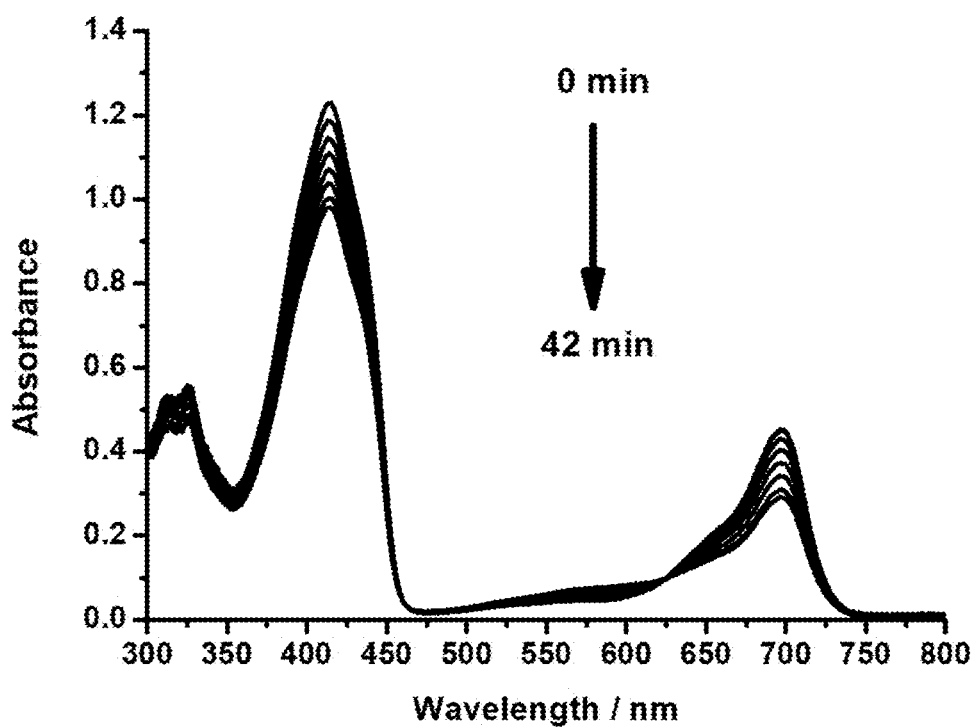
FIG. 12 shows results of a singlet oxygen yield determination experiment of the compound F-3 under ultrasound (Embodiment 14).

Embodiment 13: Singlet Oxygen Yield Determination Experiment of Compound F-3 Under Illumination The compound F-3 synthesized in Embodiment 11 was used, and F-3-DMSO solution was added into methanol and mixed evenly, then 1,3-Diphenylisobenzofuran (DPBF) was added, and a concentration of DPBF was adjusted till an absorbance value thereof was about 1.0, then a xenon lamp light source with a wavelength of 660 nanometers (adjusted by grating filter) was used to irradiate, and a ultraviolet-visible absorption curve of the system was measured at equal time intervals. A correlation curve between the absorbance and the time was drawn according to changes of the absorbance of DPBF at a wavelength of 411 nanometers, and a singlet oxygen proton yield of the compound F-3 was calculated by using methylene blue as a reference. The results are shown in FIG. 11. The figure shows changes of a UV-vis absorption spectrum of the mixed system with the extension of illumination time. According to a relevant formula, the singlet oxygen photon yield of the compound F-3 is about 0.73.

Embodiment 14: Singlet Oxygen Yield Determination Experiment of Compound F-3 Under Ultrasound The compound F-3 synthesized in Embodiment 11 was used, and F-3-DMSO solution was added into ethylene glycol monomethyl ether and mixed evenly, then 1,3-Diphenylisobenzofuran (DPBF) was added, and a concentration of DPBF was adjusted till an absorbance value of DPBF was about 1.0, then ultrasound was used to circularly simulate (1.5 W/cm$^2$, 50% duty cycle), and a ultraviolet-visible absorption curve of the system was measured at equal time intervals. A correlation curve between the absorbance and the time was drawn according to changes of the absorbance of DPBF at a wavelength of 411 namometers, and the results are shown in FIG. 11. The figure shows changes of a UV-vis absorption spectrum of the mixed system with the extension of ultrasound time. It can be seen that the compound F-3 can generate the singlet oxygen under the promotion of ultrasound.

Embodiment 15: In Vitro Cell Anti-Cancer Test of Compound F-3 Under Illumination MCF-7 (human breast cancer cell) was planted in 96-well culture plates at a density of 5000 cells per well and cultured in a cell incubator for 24 hours (37° C., 5% $CO_2$). The compound F-3 synthesized in Embodiment 11 was used, and F-1-DMSO solution was added into DMEM containing 10% fetal calf serum to prepare solutions with different concentrations, and the prepared solutions were added to the 96-well culture plates and placed in the cell incubator to incubate for 30 minutes, and then irradiated for a certain period by red light with a wavelength of 660 nanometers. After irradiation, 96 empty plates were placed in a cell incubator and continuously incubated for 12 hours. Then, 100 µl of culture medium containing 5 mg/ml MTT was added to each well, and incubated in a cell incubator for 4 hours. The culture solutions in the well of the plates were removed, 100 µl of DMSO was added to each well to fully dissolve MTT oxidation products, and then the absorbance of each well at 570 nanometers and 630 nanometers were measured with a microplate reader, and a cell survival rate was calculated. The results are shown in FIG. 11.

Figure 13:
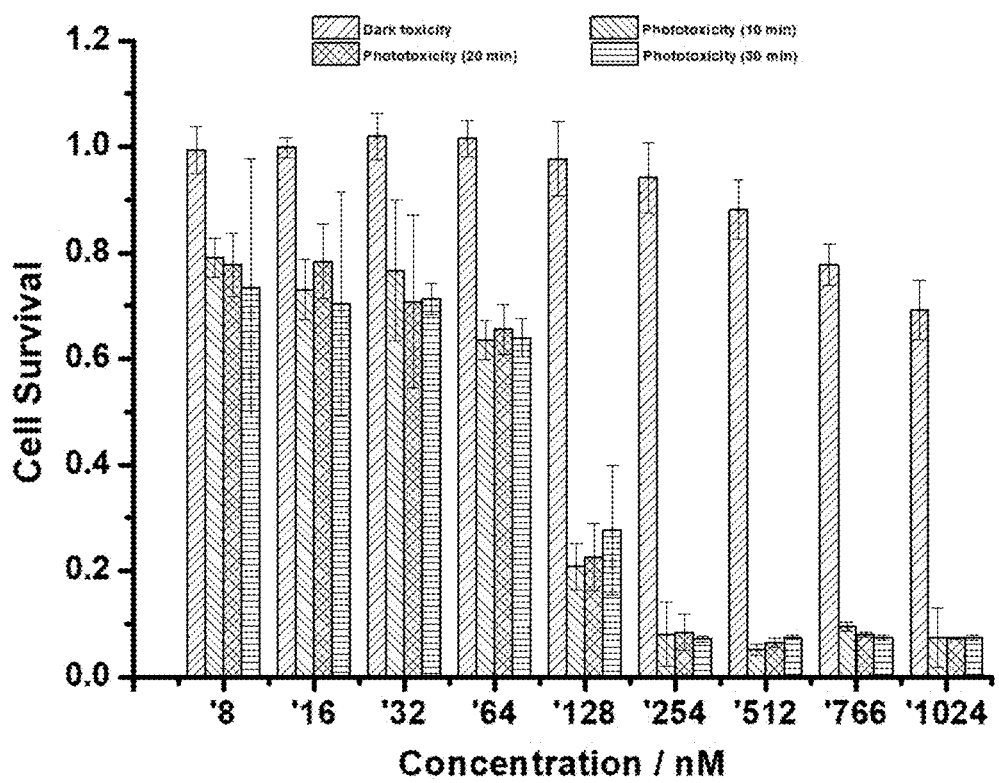
FIG. 13 shows results of an in vitro cell anti-cancer test experiment of the compound F-3 under illumination (Embodiment 15).

It can be seen from FIG. 13 that the compound F-3 has a certain killing effect on the cells without illumination due to the existence of tellurium with heavy atoms, but has poor chemical efficacy; and under illumination, the compound F-3 can produce an obvious killing effect on the cells at low energy density of illumination. It can be seen that the compound F-3 has the dual efficacy of chemotherapy and photodynamic/sonodynamic therapy for tumor cells.

Figure 14:
FIG. 14 shows a scanning electron microscope of a self-assembled nano drug-delivery system of the compound F-1 (Embodiment 16).

Embodiment 16: Test of Establishing Self-Assembled Nano Drug-Delivery System The compound F-1 synthesized in Embodiment 1 was used, and a proper amount of F-1-DMSO solution was added into a phosphate buffer (PBS) or ultrapure water as required. After shaking the mixture evenly, the compound F-1 could be self-assembled in the PBS or ultrapure water to form a nanoparticle system. A scanning electron microscope of the system is shown in FIG. 14. It can be seen from FIG. 14 that the nanoparticles formed by the self-assembly of the compound F-1 in the nano-system are about 200 nanometers in size, regular in shape and uniform in size, and have excellent dispersion properties.

What is claimed is:

1. An oxazine compound having a structural formula F:

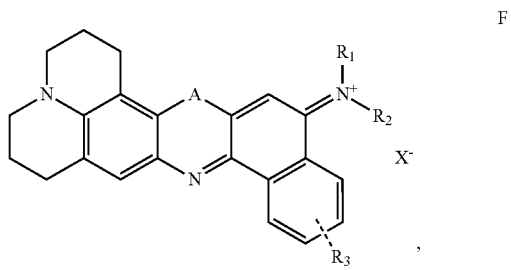

wherein,

A is selenium;

$R_1$, $R_2$, and $R_3$ are each independently selected from hydrogen, substituted $C_{1-20}$ alkyl, and unsubstituted $C_{1-20}$ alkyl;

the substituted $C_{1-20}$ alkyl is substituted by one or more functional groups selected from halogen, hydroxyl, alkoxy, aldehyde, carbonyl, amino, carboxyl, ester, acylamino, nitro, and sulfonic acid group; and X is selected from phosphate radical, sulfate, bisulfate, nitrate, chlorine anion, bromine anion, iodine anion, and perchlorate.

2. The oxazine compound according to claim 1, wherein $R_1$, $R_2$, and $R_3$ are each independently selected from hydrogen, substituted $C_{1-14}$ alkyl, and unsubstituted $C_{1-14}$ alkyl.

3. The oxazine compound according to claim 2, wherein $R_1$, $R_2$, and $R_3$ are each independently selected from hydrogen, substituted $C_{1-6}$ alkyl, and unsubstituted $C_{1-6}$ alkyl.

4. The oxazine compound according to claim 3, wherein one of $R_1$ and $R_2$ is hydrogen.

5. The oxazine compound according to claim 3, wherein $R_3$ is hydrogen.

6. The oxazine compound according to claim 1, wherein the compound is selected from

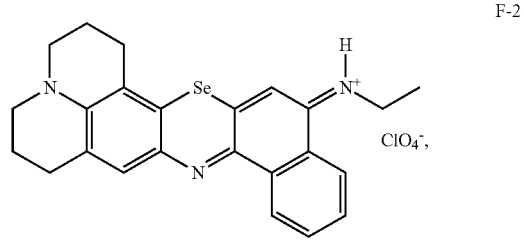

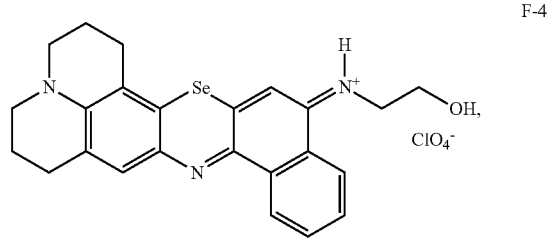

-continued

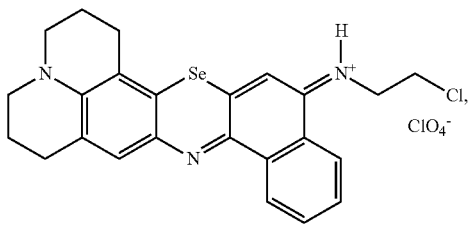

F-6

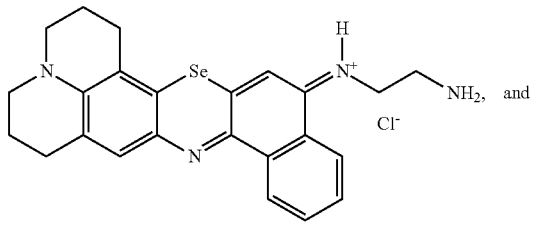

F-9

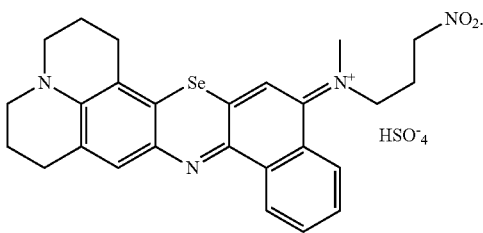

F-10

7. A photosensitizer, comprising the oxazine compound according to claim 1.

8. The photosensitizer according to claim 7, wherein the photosensitizer sensitizer is a near-infrared long-wavelength fluorescent probe.

9. The photosensitizer according to claim 8, wherein the photosensitizer comprising self-assembled nanoparticles having particle sizes of 1 to 1000 nanometers.

10. A method for inhibiting growth of cancer cells, comprising:
   activating the photosensitizer of claim 7 using a 660-wavelength red light to generate singlet oxygen; and
   exposing the cancer cells to the singlet oxygen.

11. An acoustic sensitizer, comprising the oxazine compound according to claim 1.

12. The acoustic sensitizer according to claim 11, comprising self-assembled nanoparticles having particle sizes of 1 to 1000 nanometers.

13. A method for inhibiting growth of cancer cells, comprising:
   activating the acoustic sensitizer of claim 11 using ultrasound to generate singlet oxygen; and exposing the cancer cells to the singlet oxygen.

\* \* \* \* \*